US011807862B2

(12) United States Patent
Evans et al.

(10) Patent No.: US 11,807,862 B2
(45) Date of Patent: *Nov. 7, 2023

(54) GREEN BEAN PLANTS WITH IMPROVED DISEASE RESISTANCE

(71) Applicant: Seminis Vegetable Seeds, Inc., St. Louis, MO (US)

(72) Inventors: Ellen L. Evans, St. Louis, MO (US); Kenneth Kmiecik, Madison, WI (US); Chad Kramer, Winters, CA (US); Arie Oppelaar, Ijzendoorn (NL)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/930,304

(22) Filed: Jul. 15, 2020

(65) Prior Publication Data

US 2020/0407744 A1 Dec. 31, 2020

Related U.S. Application Data

(63) Continuation-in-part of application No. 16/742,529, filed on Jan. 14, 2020, now Pat. No. 11,122,757.

(60) Provisional application No. 62/792,814, filed on Jan. 15, 2019.

(51) Int. Cl.
C12N 15/82 (2006.01)
A01N 63/22 (2020.01)

(52) U.S. Cl.
CPC ......... *C12N 15/8282* (2013.01); *A01N 63/22* (2020.01)

(58) Field of Classification Search
None
See application file for complete search history.

(56) References Cited

U.S. PATENT DOCUMENTS

| | | | |
|---|---|---|---|
| 6,060,051 A | 5/2000 | Heins et al. | |
| 6,103,228 A | 8/2000 | Heins et al. | |
| 6,291,426 B1 | 9/2001 | Heins et al. | |
| 6,417,163 B1 | 7/2002 | Heins et al. | |
| 6,638,910 B2 | 10/2003 | Heins et al. | |
| 9,801,387 B2 * | 10/2017 | Hellwege | A01N 43/713 |
| 10,349,609 B1 | 7/2019 | Wahlquist | |
| 11,122,757 B2 | 9/2021 | Evans et al. | |
| 2010/0083395 A1 | 4/2010 | Reuber et al. | |
| 2017/0121732 A1 | 5/2017 | Niblett | |
| 2018/0020628 A1 | 1/2018 | Gehin | |
| 2020/0221659 A1 | 7/2020 | Evans et al. | |
| 2022/0030789 A1 | 2/2022 | Evans et al. | |

FOREIGN PATENT DOCUMENTS

WO 2016149352 9/2016

OTHER PUBLICATIONS

Genchev et al. Bulgarian Journal of Agricultural Science (2002), 8:181-187.*
USPTO: Non-Final Office Action regarding U.S. Appl. No. 16/742,529, dated Oct. 15, 2020.
USPTO: Response to Non-Final Office Action regarding U.S. Appl. No. 16/742,529, filed Jan. 13, 2021.
USPTO: Final Office Action regarding U.S. Appl. No. 16/742,529, dated Mar. 9, 2021.
USPTO: Response to Final Office Action regarding U.S. Appl. No. 16/742,529, filed Apr. 26, 2021.
USPTO: Notice of Allowance regarding U.S. Appl. No. 16/742,529, dated May 26, 2021.
U.S. Appl. No. 17/390,526, filed Jul. 30, 2021, Evans et al.
International Preliminary Report on Patentability regarding International Application No. PCT/US2020/013338, dated Jun. 16, 2021.
Antonio, et al., "Genetic Control of The Resistance of Common Beans to White Mold Using The Reaction to Oxalic Acid", Genetics And Molecular Research 7(3) 733-40, 2008.
Genchev, D. and I. Kiryakov, Inheritance of Resistance to White Mold Disease (*Sclerotinia sclerotiorum* (Lib.) de Bary) in A 195 (*Phaseolus vulgaris* L.), Bulg. J. Agric. Sci., 2002, 181-187, 8.
Jacob, et al., Advances in Breeding And Biotechnology of Legume Crops, Plant Cell Tiss Organ Cult, 2016, 561-584, 127.
Lehner, et al., Adaption and Resistance to Diseases in Brazil of Putative Sources of Common Bean Resistance to White Mold, Plant Disease, 2015, 1098-1103, 99(8).
Mamidi, et al., Sequence-Based Introgression Mapping Identifies Candidate White Mold Tolerance Genes in Common Bean, Plant Genome, 2016, 1-11, 9(2).
Maxwell, et al., Quantitative Trait Loci Linked to White Mold Resistance in Common Bean, Crop Sci., 2007, 2285-2294, 47.
Miklas, et al., QTL Conditioning Physiological Resistance and Avoidance to White Mold in Dry Bean, Crop Sci., 2001, 309-315, 41.
Miklas, P. N., Marker-Assisted Backcrossing QTL for Partial Resistance to Sclerotinia White Mold in Dry Bean, Crop Science, 2007, 935-942, 47.
Mkwaila, et al., Identification of QTL For Agronomic Traits And Resistance to White Mold in Wild And Landrace Germplasm of Common Bean, Plant Breeding, 2011, 665-672, 130.
Perez-Vega, et al., Mapping Quantitative Trait Loci Conferring Partial Physiological Resistance to White Mold in The Common Bean RIL Population Xana X Cornell 49242, Mol. Breeding, 2012, 31-41, 29.
Poryazov, et al., New Garden Bean Cultivar For Fresh Market, Proc. IVth Balkan Symp. on Vegetables and Potatoes, 2009, 151-154, Acta Hort. 830, ISHS.
Schmutz, et al., A Reference Genome For Common Bean And Genome-Wide Analysis of Dual Domestications, Nature Genetics, 2014, 707-713, 46.

(Continued)

*Primary Examiner* — Medina A Ibrahim
(74) *Attorney, Agent, or Firm* — DENTONS US LLP; Alissa Eagle

(57) ABSTRACT

Green bean plants exhibiting resistance to *Sclerotinia sclerotiorum* are provided, together with kits and methods for controlling *Sclerotinia sclerotiorum* infection. Such methods include the application of fungicidal *Bacillus subtilis* strains to plants exhibiting resistance to *Sclerotinia sclerotiorum*.

25 Claims, 2 Drawing Sheets

Specification includes a Sequence Listing.

(56) References Cited

OTHER PUBLICATIONS

Schwartz, et al., Breeding Common Bean for Resistance to White Mold: A Review, Crop Sci., 1832-1844, 53.
Singh, et al., Introgressing White Mold Resistance From Phaseolus Coccineus PI 439534 to Common Pinto Bean, Crop Sci., 2014, 1026-1032, 54(3).
Singh, et al., Registration of Common Bean Pinto PRP 153 And VCP 13 With High Levels of Broad-Spectrum White Mold Resistance, Journal of Plant Registrations, 2016, 291-295, 10.
Singh, et al., Registration of White Mold Resistant Dry Bean Germplasm Line A 195, Journal of Plant Registrations, 2007, 62-63, 1.
Soule, et al., Comparative QTL Map For White Mold Resistance in Common Bean, And Characterization of Partial Resistance in Dry Bean Lines VA19 And I9365-31, Crop Sci., 2011, 123-139, 51.
Souza, et al., White Mold Resistance-Associated Quantitative Trait Loci in The Jalo x Small White Common Bean Population, Genet Mol Res., Aug. 26, 2016, 1-15, 15(3).
Vasconcellos, et al., Meta-QTL For Resistance to White Mold in Common Bean. PLOS One, 2017, e0171685, 12 (2).
Viteri, et al., Inheritance of White Mold Resistance in an Andean Common Bean A 195 And Its Relationship With Andean G 122, Crop Science, 2015, 10.2135/cropsci2014.02.0145, 55. 44.
International Search Report and Written Opinion regarding International Application No. PCT/US2020/013338, dated Apr. 27, 2020.
Pascual et al., "Screening Common Bean for Resistance to Four Sclerotinia sclerotiorum Isolates Collected in Northern Spain," Plant Disease, 2010, 94(7):885-890.
Chauhan et al., "Screening and Identification of Resistant Sources Against Sclerotinia sclerotiorum causing White Mold Disease in Common Bean," 2020, Crop Science, 60(4):1986-1996, ISSN: 011-183X, .doi.org/10.1002/csc2.20160.
Carneiro, et al., "Genetics of Common Bean Resistance to White Mold," Brazilian Society of Plant Breeding printed in Brazil, Crop Breeding and Applied Technology, 2011, pp. 165-173. Retrieved from the Internet: URL:https:www.scielo.br/pdf/cbab/v11n2/0.9.pdf.
Ender, et al., "Identification of QTL Associated with White Mold Resistance in Common Bean," Crop Science, 2005, 45(6):2482-2490.
Anonymous:VUK092D02.F "VUK Phaseolus vulgaris genomic 5, genomic survey sequence—Nucleotide-NCBI," 2013, Retrieved from the Internet: URL:https://www.ncbi.nlm.nih.gov/nuccore/JY831945, [retrieved on May 5, 2020].
Anonymous:VUK237K07.F "VUK Phaseolus vulgaris genomic 5, genomic survey sequence—Nucleotide-NCBI," 2013, Retrieved from the Internet: URL:https://www.ncbi.nlm.nih.gov/nuccore/JY770634, [retrieved on May 5, 2020].
Extended European Search Report Regarding European Application No. 20151905.5 dated May 13, 2020.
Schaeffer, et al. "Fusion of Bacterial Protoplasts," PNAS, 1976, 73(6):2151-2155.
Ender et al. Marker-assisted selection for white mold resistance in common bean, Mol. Breeding 21:149-157, 2008.
European Search Report and Opinion regarding European App. No. 21185381.7, dated Dec. 12, 2021.
USPTO: Third Party Submission, including Concise Statement of Relevance, regarding U.S. Appl. No. 17/390,526, 18 pages, dated Aug. 12, 2022.
USPTO: Third Party Submission, including Concise Statement of Relevance, regarding U.S. Appl. No. 17/390,526, 21 pages, dated Aug. 12, 2022.
*SRR 13151543 Outlaw* vs. *SEQ ID No. 26 Alignment*, submitted in Third Party Submission regarding U.S. Appl. No. 17/390,526 dated Aug. 12, 2022.
*SRR 13151543 Outlaw* vs. *SEQ ID No. 14 Alignment*, submitted in Third Party Submission regarding U.S. Appl. No. 17/390,526 dated Aug. 12, 2022.
*SRR 13151543 Outlaw* vs. *SEQ ID No. 20 Alignment*, submitted in Third Party Submission regarding U.S. Appl. No. 17/390,526 dated Aug. 12, 2022.
*SRR 13151543 Outlaw* vs. *SEQ ID No. 2 Alignment*, submitted in Third Party Submission regarding U.S. Appl. No. 17/390,526 dated Aug. 12, 2022.
*SRR 13151543 Outlaw* vs. *SEQ ID No. 8 Alignment*, submitted in Third Party Submission regarding U.S. Appl. No. 17/390,526 dated Aug. 12, 2022.
NCBI Whole Genome Sequence of phaseolus vulgaris:Outlaw (SRR13151543), available at https:// trace.ncbi.nlm.nih.gov/Traces/index.html?view=run_browser&acc=SRR13151543&display=download, submitted in Third Party Submission regarding U.S. Appl. No. 17/390,526 dated Aug. 12, 2022.
NCBI Whole Genome Sequence of phaseolus vulgaris: Tema (SRR13151522), available at https:// trace.ncbi.nlm.nih.gov/Traces/index.html?view=run_browser&acc=SRR13151522&display=download, submitted in Third Party Submission regarding U.S. Appl. No. 17/390,526 dated Aug. 12, 2022.
*SRR 13151522 Tema* vs. *SEQ ID No. 2 Alignmen*, submitted in Third Party Submission regarding U.S. Appl. No. 17/390,526 dated Aug. 12, 2022.
*SRR 13151522 Tema* vs. *SEQ ID No. 8 Alignment*, submitted in Third Party Submission regarding U.S. Appl. No. 17/390,526 dated Aug. 12, 2022.
*SRR 13151522 Tema* vs. *SEQ ID No. 14 Alignment*, submitted in Third Party Submission regarding U.S. Appl. No. 17/390,526 dated Aug. 12, 2022.
*SRR 13151522 Tema* vs. *SEQ ID No. 20 Alignment*, submitted in Third Party Submission regarding U.S. Appl. No. 17/390,526 dated Aug. 12, 2022.
*SRR 13151522 Tema* vs. *SEQ ID No. 26 Alignment*, submitted in Third Party Submission regarding U.S. Appl. No. 17/390,526 dated Aug. 12, 2022.
Agarwal, et al. Whole-genome sequencing and phenotyping revealed structural variants and varied level of resistance against leaf crumple disease in diverse lines of snap bean (Phaseolus vulgaris), doi: 10.20944/10.20944/ preprints202010.0501.v1, www.preprints.org, 2020.
Meseyton, Loving that Tema Green Bean, Grainviews, 2015.
Syngenta, Screen Shots from YouTube Promotional Video on Outlaw Fresh Market Bean, submitted in Third Party Submission regarding U.S. Appl. No. 17/390,526 dated Aug. 12, 2022.
United States Plant Variety Protection Certificate for Variety Tema, Certificate No. 8900152, 1992.
Restriction Requirement regarding U.S. Appl. No. 17/390,526, dated Jan. 4, 2023.

\* cited by examiner

SEQUENCE LISTING

```
<160> NUMBER OF SEQ ID NOS: 26

<210> SEQ ID NO 1
<211> LENGTH: 101
<212> TYPE: DNA
<213> ORGANISM: Phaseolus vulgaris L.

<400> SEQUENCE: 1
aggacctgca aaatgcatca aaatttaagg gagatgaccc agaaagaatc tacacgcaag      60
ggtaacatga aatagacaat tgccttttta tattagaaac a                        101

<210> SEQ ID NO 2
<211> LENGTH: 301
<212> TYPE: DNA
<213> ORGANISM: Phaseolus vulgaris L.
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (214)..(215)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t

<400> SEQUENCE: 2
```

```
gtctgcagat gttatnggaa agcagaaact cttttcacta attttacgag gtatcctcaa    60
gaaattttaa ttgttttga attaattgga ttcatctggg tcacagttga gtgtttgagg   120
gctgtgataa atccatnctt catatgaatc acactttatg taagggacta agcaaaatga   180
agaatactcc agatgttcng cnaaaatcat gaannaaaat gtgcagtttt actgcagaac   240
agaaagttaa gactggtgtn ttccaaatgt tgcatcgaaa gtgggattac ttttgtccca   300
a                                                                  301
```

```
<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgtttgaggg ctgtgataaa tccat                                         25
```

```
<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
gaacatctgg agtattcttc attttgct                                      28
```

```
<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
cttcatatga atcacacttt                                               20
```

```
<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
cttcatatga atcgcacttt                                               20
```

```
<210> SEQ ID NO 7
<211> LENGTH: 237
<212> TYPE: DNA
<213> ORGANISM: Phaseolus vulgaris L.

<400> SEQUENCE: 7
ccaatgcagc ttctgatgcg atcccacttg aaggagcttc taacccttcg acgaaggaac    60
ccagaaaagt cattcatgtg atattgcaag taagcccggt cagcttcaat gttgccatga   120
cctcgaagcg tcaccatgta aacaaacccc acaagacaca ctagcagtat caccagcacc   180
agcatggcaa cgaggtacac tacgaggagc catgtgactc tgaaaaaggc tccaatg      237
```

```
<210> SEQ ID NO 8
```

```
<211> LENGTH: 121
<212> TYPE: DNA
<213> ORGANISM: Phaseolus vulgaris L.

<400> SEQUENCE: 8
caaagcactt ctaattacat ctcaagtcct cattacaagc ttccaataaa cacaaacttg    60
aaatttgaaa ctttgtttcc cttacatgtt gcacatattg atgaataaac acatgtaatt   120
a                                                                  121

<210> SEQ ID NO 9
<211> LENGTH: 121
<212> TYPE: DNA
<213> ORGANISM: Phaseolus vulgaris L.

<400> SEQUENCE: 9
taaataacaa gcactcattg cactgcattc gatgtgccac ccaggtcttc caggacccca    60
agggctgtcc caactaggct cacctggttt agcagcctgc aattattatt attaagaaat   120
a                                                                  121

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
gccacccagg tcttcca                                                  17

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gctaaaccag gtgagcctag t                                             21

<210> SEQ ID NO 12
<211> LENGTH: 16
<212> TYPE: DNA
<213> ORGANISM: Artificial Sequence
<220> FEATURE:
<223> OTHER INFORMATION: Probe

<400> SEQUENCE: 12
tgggacagcc cttggg                                                   16

<210> SEQ ID NO 13
<211> LENGTH: 16
<212> TYPE: DNA
<213> ORGANISM: Artificial sequence
<220> FEATURE:
<223> OTHER INFORMATION: Probe

<400> SEQUENCE: 13
tgggacagcc cctggg                                                   16

<210> SEQ ID NO 14
<211> LENGTH: 121
<212> TYPE: DNA
<213> ORGANISM: Phaseolus vulgaris L.
```

```
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t

<400> SEQUENCE: 14
atctcctcct tctcctccta catattcccc ttnctccagt tatgatataa tcccctttc      60 aaaccaaatt tgccatctgc ccatcctgtt attataccca tcattctacc anaaatccct   120
g                                                                   121

<210> SEQ ID NO 15
<211> LENGTH: 97
<212> TYPE: DNA
<213> ORGANISM: Phaseolus vulgaris L.
<220> FEATURE:
<221> NAME/KEY: misc_feature
<222> LOCATION: (97)..(97)
<223> OTHER INFORMATION: n is a, c, g, or t

<400> SEQUENCE: 15
gctgaaattg ttgagaaggt gaaggaaagg gagggttgtg atgagaaatc ttccagtaat    60
gaggttgaaa ttaagcactc ggaaaatgag gaggggn                             97

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
gctgaaattg ttgagaaggt gaagga                                         26

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
tccgagtgct taatttcaac ctcat                                          25

<210> SEQ ID NO 18
<211> LENGTH: 16
<212> TYPE: DNA
<213> ORGANISM: Artificial Sequence
<220> FEATURE:
<223> OTHER INFORMATION: Probe

<400> SEQUENCE: 18
ctcatcacaa ccctcc                                                    16

<210> SEQ ID NO 19
<211> LENGTH: 16
<212> TYPE: DNA
<213> ORGANISM: Artificial Sequence
<220> FEATURE:
<223> OTHER INFORMATION: Probe

<400> SEQUENCE: 19
```

```
ctcatcacca ccctcc                                                           16
```

```
<210> SEQ ID NO 20
<211> LENGTH: 326
<212> TYPE: DNA
<213> ORGANISM: Phaseolus vulgaris L.
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t

<400> SEQUENCE: 20
ccatnnggga gttgagtcat gtttagaagt gtattaccta gctcttgatt gctgantngc           60
ctcactaact ctgcttaagc gtatttggat ttgtgntgtc ggtcggcgta acgagcgagt          120
tcgagacatg atctcgatcg tgcagactct atcaggacac ttgcccctag gctcaaggat         180
gattaatccg aagagtcttt gtccaagncc gatgtgacga ttgggcttcc cgaggtctga         240
agtgacattg ggcggcacct ggtcgagtga tgtgatgtgc attaatgagg gatttttggg        300
cgccatttga tgagggtcat tggatc                                              326
```

```
<210> SEQ ID NO 21
<211> LENGTH: 121
<212> TYPE: DNA
<213> ORGANISM: Phaseolus vulgaris L.
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 21
gttttaaata tggcttaata gtaacttagt gcttcctctt ttatcgacta agttgtaggc          60
atatcttgtg aataactcaa ttttatattc tgaagttggt gaaaanttaa aaanctaaga        120
a                                                                         121
```

```
<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
ggcttaatag taacttagtg cttcctctt                                            29
```

```
<210> SEQ ID NO 23
<211> LENGTH: 32
```

```
<212> TYPE: DNA
<213> ORGANISM: Artificial Sequence
<220> FEATURE:
<223> OTHER INFORMATION: Primer

<400> SEQUENCE: 23
ttttcaccaa cttcagaata taaaattgag tt                                32

<210> SEQ ID NO 24
<211> LENGTH: 18
<212> TYPE: DNA
<213> ORGANISM: Artificial Sequence
<220> FEATURE:
<223> OTHER INFORMATION: Probe

<400> SEQUENCE: 24
aagttgtagg catatctt                                                18

<210> SEQ ID NO 25
<211> LENGTH: 18
<212> TYPE: DNA
<213> ORGANISM: Artificial Sequence
<220> FEATURE:
<223> OTHER INFORMATION: Probe

<400> SEQUENCE: 25
aagttgtagg cctatctt                                                18

<210> SEQ ID NO 26
<211> LENGTH: 121
<212> TYPE: DNA
<213> ORGANISM: Phaseolus vulgaris L.
<220> FEATURE:
<221> NAME/KEY: misc_feature
<222> LOCATION: (85)..(85)
<223> OTHER INFORMATION: n is a, c, g, or t

<400> SEQUENCE: 26
tcacgagctg ggttgttcaa atgtggcttg cacagatgac aagcaattcg ggagagctat  60
aaatgcagcc cagcaagcag atgcnactgt gctggtgatg ggcctggatc agtccatcga  120
g                                                                  121
```

GREEN BEAN PLANTS WITH IMPROVED DISEASE RESISTANCE

CROSS-REFERENCE TO RELATED APPLICATIONS

This application is a continuation-in-part of U.S. application Ser. No. 16/742,529, filed Jan. 14, 2020, which claims the priority of U.S. Provisional Appl. Ser. No. 62/792,814, filed Jan. 15, 2019, the entire disclosure of all of which are incorporated herein by reference.

INCORPORATION OF SEQUENCE LISTING

A sequence listing containing the file named "SEMB036US-revised_ST25.txt" which is 8.0 kilobytes (measured in MS-Windows®) and created on Mar. 26, 2020, and comprises 26 sequences, is incorporated herein by reference in its entirety.

FIELD OF THE INVENTION

The present invention relates to the field of agriculture and more specifically to methods and compositions for providing improved disease resistance in beans.

BACKGROUND

Disease resistance is an important trait in agriculture, particularly for the production of food crops. Although disease resistance alleles have been identified in beans, efforts to introduce these alleles into cultivated lines have been hindered by a lack of specific markers linked to the alleles, as well as the presence of deleterious alleles genetically linked to disease resistance alleles that lead to an unacceptable reduction in yield, fruit size, and fruit quality. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an incomplete understanding of the genetic background underlying expression of a desired phenotype. In the absence of accurate and validated markers for use in MAS, it may not be feasible to produce new plant lines exhibiting certain disease resistance phenotypes and acceptable yield, fruit size, and fruit quality.

SUMMARY

In one aspect, the present invention provides a green bean plant comprising a recombinant chromosomal segment on chromosome 2, wherein said recombinant chromosomal segment comprises an allele conferring resistance to *Sclerotinia sclerotiorum* relative to a plant lacking said recombinant chromosomal segment. In some embodiments, said recombinant chromosomal segment comprises a marker locus selected from the group consisting of a marker locus M1 (SEQ ID NO: 1), marker locus M2 (SEQ ID NO: 7), and marker locus M3 (SEQ ID NO: 2) on chromosome 2. In certain embodiments, said plant further comprises a recombinant chromosomal segment on chromosome 7, wherein said recombinant chromosomal segment on chromosome 7 comprises marker locus M9 (SEQ ID NO: 8) and marker locus M10 (SEQ ID NO: 14) or marker locus M11 (SEQ ID NO: 20) and marker locus M12 (SEQ ID NO: 26). In further embodiments, said recombinant chromosomal segment on chromosome 7 lacks a deleterious allele genetically linked thereto that confers an undesirable color to a seed produced by the plant. In yet further embodiments, said recombinant chromosomal segment comprises a favorable allele associated with desirable seed color at marker locus M6 (SEQ ID NO: 15) and a favorable allele associated with *Sclerotinia sclerotiorum* resistance at marker locus M11 (SEQ ID NO: 20) and marker locus M12 (SEQ ID NO: 26) on chromosome 7. In some embodiments, the green bean plant comprising a recombinant chromosomal segment on chromosome 2, wherein said recombinant chromosomal segment comprises an allele conferring resistance to *Sclerotinia sclerotiorum* relative to a plant lacking said recombinant chromosomal segment is further defined as an inbred or hybrid plant. In other embodiments, said *Sclerotinia sclerotiorum* resistance allele is located between 23,719,195 bp and 27,452,157 bp on chromosome 2 of the *P. vulgaris* reference genome sequence v. 1.0.

In another aspect, the present invention provides a green bean plant comprising a recombinant chromosomal segment on chromosome 7, wherein said recombinant chromosomal segment comprises an allele conferring resistance to *Sclerotinia sclerotiorum* relative to a plant lacking said recombinant chromosomal segment. In one embodiment, said recombinant chromosomal segment comprises a marker locus selected from the group consisting of marker locus M11 (SEQ ID NO: 20), marker locus M8 (SEQ ID NO: 21), and marker locus M12 (SEQ ID NO: 26) on chromosome 7. In another embodiment, said recombinant chromosomal segment on chromosome 7 lacks a deleterious allele genetically linked thereto that confers an undesirable color to a seed produced by the plant. In a further embodiment, said recombinant chromosomal segment comprises a favorable allele associated with desirable seed color at marker locus M6 (SEQ ID NO: 15) and a favorable allele associated with *Sclerotinia sclerotiorum* resistance at marker locus M11 (SEQ ID NO: 20) and marker locus M12 (SEQ ID NO: 26) on chromosome 7. In some embodiments, said introgressed *Sclerotinia sclerotiorum* resistance allele is located between 42,414,123 bp and 45,411,236 bp on chromosome 7 of the *P. vulgaris* reference genome sequence v. 1.0. In other embodiments, said green bean plant comprising a recombinant chromosomal segment on chromosome 7, wherein said recombinant chromosomal segment comprises an allele conferring resistance to *Sclerotinia sclerotiorum* relative to a plant lacking said recombinant chromosomal segment is an inbred or hybrid. In a further embodiment, said plant comprises said chromosomal segment.

In another aspect, the present invention provides a recombinant DNA segment comprising a *Sclerotinia sclerotiorum* resistance allele that confers to a plant increased resistance to *Sclerotinia sclerotiorum*, wherein the allele lacks a deleterious allele genetically linked thereto that confers to a plant undesirable seed color. In some embodiments, said *Sclerotinia sclerotiorum* resistance allele is derived from a plant of bean line G122 or A195. In other embodiments, said recombinant DNA segment comprises a sequence selected from the group consisting of SEQ ID NOs: 15, 20, 21, and 26. In further embodiments, said recombinant DNA segment is further defined as comprised within a plant, plant part, plant cell, or seed. In yet further embodiments, said DNA segment confers increased resistance to *Sclerotinia sclerotiorum* to said plant.

In another aspect, the present invention provides a method for producing a green bean plant with increased resistance to

*Sclerotinia sclerotiorum* comprising: crossing a green bean plant comprising a recombinant chromosomal segment on chromosome 2 or chromosome 7, wherein said recombinant chromosomal segment comprises an allele conferring resistance to *Sclerotinia sclerotiorum* relative to a plant lacking said recombinant chromosomal segment, with itself or with a second green bean plant of a different genotype to produce one or more progeny plants; and b) selecting a progeny plant comprising said *Sclerotinia sclerotiorum* resistance allele. In some embodiments, said selecting said progeny plant comprises detecting a marker locus genetically linked to said *Sclerotinia sclerotiorum* resistance allele. In other embodiments, selecting said progeny plant comprises detecting a marker locus within or genetically linked to a chromosomal segment flanked in the genome of said plant by: (a) marker locus M1 (SEQ ID NO: 1) and marker locus M2 (SEQ ID NO: 7) on chromosome 2; (b) marker locus M9 (SEQ ID NO: 8) and marker locus M10 (SEQ ID NO: 14) on chromosome 7; or (c) marker locus M11 (SEQ ID NO: 20) and marker locus M12 (SEQ ID NO: 26) on chromosome 7; wherein said introgressed *Sclerotinia sclerotiorum* resistance allele confers to said plant increased resistance to *Sclerotinia sclerotiorum* compared to a plant not comprising said allele, and wherein said plant lacks a deleterious allele genetically linked to said *Sclerotinia sclerotiorum* resistance allele that confers undesirable seed color to said plant when present. In some embodiments, selecting a progeny plant comprises detecting nucleic acids comprising marker locus M1 (SEQ ID NO: 1), marker locus M2 (SEQ ID NO: 7), marker locus M3 (SEQ ID NO: 2), marker locus M9 (SEQ ID NO: 8), marker locus M4 (SEQ ID NO: 9), marker locus M10 (SEQ ID NO: 14), marker locus M6 (SEQ ID NO: 15), marker locus M11 (SEQ ID NO: 20), marker locus M8 (SEQ ID NO: 21), or marker locus M12 (SEQ ID NO: 26). In other embodiments, said *Sclerotinia sclerotiorum* resistance allele is identified by detecting a recurrent parent allele at marker locus M6 (SEQ ID NO: 15), a non-recurrent parent allele at marker locus M11 (SEQ ID NO: 20), and a non-recurrent parent allele at marker locus M12 (SEQ ID NO: 26) on chromosome 7. In further embodiments, the progeny plant is an $F_2$-$F_6$ progeny plant. In some embodiments, producing said progeny plant comprises backcrossing.

In one aspect, the present invention provides a method of producing a plant of a green bean line exhibiting resistance to *Sclerotinia sclerotiorum*, comprising introgressing into a plant a *Sclerotinia sclerotiorum* resistance allele within a recombinant chromosomal segment flanked in the genome of said plant by: (a) marker locus M1 (SEQ ID NO: 1) and marker locus M2 (SEQ ID NO: 7) on chromosome 2; (b) marker locus M9 (SEQ ID NO: 8) and marker locus M10 (SEQ ID NO: 14) on chromosome 7; or (c) marker locus M11 (SEQ ID NO: 20) and marker locus M12 (SEQ ID NO: 26) on chromosome 7; wherein said introgressed *Sclerotinia sclerotiorum* resistance allele confers to said plant increased resistance to *Sclerotinia sclerotiorum* compared to a plant not comprising said allele, and wherein said plant lacks a deleterious allele genetically linked to said *Sclerotinia sclerotiorum* resistance allele that confers undesirable seed color to said plant when present. In some embodiments, said introgressed *Sclerotinia sclerotiorum* resistance allele is within a recombinant chromosomal segment flanked in the genome of said plant by marker locus M1 (SEQ ID NO: 1) and marker locus M2 (SEQ ID NO: 7) on chromosome 2, and wherein said plant further comprises a further introgressed *Sclerotinia sclerotiorum* resistance allele within a recombinant chromosomal segment flanked in the genome of said plant by marker locus M9 (SEQ ID NO: 8) and marker locus M10 (SEQ ID NO: 14) on chromosome 7 or marker locus M11 (SEQ ID NO: 20) and marker locus M12 (SEQ ID NO: 26) on chromosome 7. In other embodiments, said recombinant chromosomal segment is flanked in the genome of said plant by marker locus M11 (SEQ ID NO: 20) and marker locus M12 (SEQ ID NO: 26) on chromosome 7. In some embodiments, said recombinant chromosomal segment is defined by a recurrent parent allele at marker locus M6 (SEQ ID NO: 15), a non-recurrent parent allele at marker locus M11 (SEQ ID NO: 20), and a non-recurrent parent allele at marker locus M12 (SEQ ID NO: 26) on chromosome 7. In other embodiments, said introgressing comprises backcrossing, marker-assisted selection, or assaying for said *Sclerotinia sclerotiorum* resistance. The invention further provides green bean plants obtainable by the methods provided herein.

In another aspect, the present invention provides a method of selecting a green bean plant with increased resistance to *Sclerotinia sclerotiorum* comprising: crossing a green bean plant comprising a recombinant chromosomal segment on chromosome 2 or chromosome 7, wherein said recombinant chromosomal segment comprises an allele conferring resistance to *Sclerotinia sclerotiorum* relative to a plant lacking said recombinant chromosomal segment, with itself or with a second green bean plant of a different genotype to produce one or more progeny plants; and b) selecting a progeny plant comprising said *Sclerotinia sclerotiorum* resistance allele. In some embodiments, selecting said progeny plant comprises detecting a marker locus genetically linked to said *Sclerotinia sclerotiorum* resistance allele. In other embodiments, selecting said progeny plant comprises detecting a marker locus within or genetically linked to a chromosomal segment flanked in the genome of said plant by: (a) marker locus M1 (SEQ ID NO: 1) and marker locus M2 (SEQ ID NO: 7) on chromosome 2; (b) marker locus M9 (SEQ ID NO: 8) and marker locus M10 (SEQ ID NO: 14) on chromosome 7; or (c) marker locus M11 (SEQ ID NO: 20) and marker locus M12 (SEQ ID NO: 26) on chromosome 7. In some embodiments, selecting a progeny plant comprises detecting nucleic acids comprising marker locus M1 (SEQ ID NO: 1), marker locus M2 (SEQ ID NO: 7), marker locus M3 (SEQ ID NO: 2), marker locus M9 (SEQ ID NO: 8), marker locus M4 (SEQ ID NO: 9), marker locus M10 (SEQ ID NO: 14), marker locus M6 (SEQ ID NO: 15), marker locus M11 (SEQ ID NO: 20), marker locus M8 (SEQ ID NO: 21), and marker locus M12 (SEQ ID NO: 26). In other embodiments, said progeny plant is an $F_2$-$F_6$ progeny plant. In further embodiments, producing said progeny plant comprises backcrossing.

In one aspect, a kit is provided herein comprising (a) a bean plant, plant part, or plant seed comprising a recombinant chromosomal segment on chromosome 2 or chromosome 7, wherein the recombinant chromosomal segment comprises an allele conferring resistance to *Sclerotinia sclerotiorum* relative to a plant lacking said recombinant chromosomal segment; and (b) at least one cell of *Bacillus subtilis* strain QST7131, or a fungicidal variant thereof. In one embodiment, the bean plant, plant part, or plant seed comprises a first recombinant chromosomal segment on chromosome 2 and a second recombinant chromosomal segment on chromosome 7, wherein the recombinant chromosomal segments comprise an allele conferring resistance to *Sclerotinia sclerotiorum* relative to a plant lacking said recombinant chromosomal segment. In another embodiment, the recombinant chromosomal segment comprises a marker locus selected from the group consisting of a marker locus M1 (SEQ ID NO: 1), marker locus M2 (SEQ ID NO:

7), and marker locus M3 (SEQ ID NO: 2) on chromosome 2. In some embodiments, the second recombinant chromosomal segment comprises marker locus M9 (SEQ ID NO: 8) and marker locus M10 (SEQ ID NO: 14) or marker locus M11 (SEQ ID NO: 20) and marker locus M12 (SEQ ID NO: 26). In other embodiments, the second recombinant chromosomal segment on chromosome 7 lacks a deleterious allele genetically linked thereto that confers an undesirable color to a seed produced by the plant. In still other embodiments, the second recombinant chromosomal segment comprises a favorable allele associated with desirable seed color at marker locus M6 (SEQ ID NO: 15) and a favorable allele associated with *Sclerotinia sclerotiorum* resistance at marker locus M11 (SEQ ID NO: 20) and marker locus M12 (SEQ ID NO: 26) on chromosome 7. In one embodiment, the *Sclerotinia sclerotiorum* resistance allele is located between 23,719,195 bp and 27,452,157 bp on chromosome 2 of the *P. vulgaris* reference genome sequence v. 1.0. In one embodiment, the recombinant chromosomal segment comprises a favorable allele associated with desirable seed color at marker locus M6 (SEQ ID NO: 15) and a favorable allele associated with *Sclerotinia sclerotiorum* resistance at marker locus M11 (SEQ ID NO: 20) and marker locus M12 (SEQ ID NO: 26) on chromosome 7. In another embodiment, the *Sclerotinia sclerotiorum* resistance allele is located between 42,414,123 bp and 45,411,236 bp on chromosome 7 of the *P. vulgaris* reference genome sequence v. 1.0. The cell of the kit may be comprised, for example, in an agriculturally acceptable carrier. Examples of agricultural carriers include but are not limited to a liquid, gel, slurry, or powder. In specific embodiments, the kit comprises a seed having been coated with a composition comprising at least one cell of *Bacillus subtilis* strain QST7131, or a fungicidal variant thereof.

In another aspect, the disclosure provides, a composition comprising (a) a bean plant, plant part, or plant seed comprising a recombinant chromosomal segment on chromosome 2 or chromosome 7, wherein the recombinant chromosomal segment comprises an allele conferring resistance to *Sclerotinia sclerotiorum* relative to a plant lacking said recombinant chromosomal segment; and (b) at least one cell of *Bacillus subtilis* strain QST7131, or a fungicidal variant thereof. In one embodiment, the cell is comprised in an agriculturally acceptable carrier.

In still another aspect, the disclosure provides a bean plant, plant part, or plant seed having applied or coated on at least a portion of the plant, plant part, or plant seed a composition comprising at least one cell of *Bacillus subtilis* strain QST7131, or a fungicidal variant thereof, wherein said plant, plant part, or plant seed comprises a recombinant chromosomal segment on chromosome 2 or chromosome 7, wherein the recombinant chromosomal segment comprises an allele conferring resistance to *Sclerotinia sclerotiorum* relative to a plant lacking said recombinant chromosomal segment. In one embodiment, the composition comprises an agriculturally acceptable carrier.

In still yet another aspect, the disclosure provides a method for controlling *Sclerotinia sclerotiorum* infection, the method comprising applying a composition comprising at least one cell of *Bacillus subtilis* strain QST7131, or a fungicidal variant thereof, to a bean plant, plant part, plant seed, or growth medium associated therewith, wherein said plant, plant part, or plant seed comprises a recombinant chromosomal segment on chromosome 2 or chromosome 7, wherein the recombinant chromosomal segment comprises an allele conferring resistance to *Sclerotinia sclerotiorum* relative to a plant lacking said recombinant chromosomal segment. In one embodiment, the growth medium is soil. In another embodiment, the composition is applied to the growth medium before, simultaneously with, or after the plant, plant part, or plant seed is planted in the growth medium. In some embodiments, applying comprises solid matrix priming, imbibing, coating, spraying, tumbling, agitating, dripping, soaking, immersing, dusting, drenching or encapsulating with the composition. In one embodiment, applying comprises applying directly to the foliar tissues of a plant. In another embodiment, the composition is a liquid, gel, slurry, or powder. In yet another embodiment, the method is further defined as comprising identifying the bean plant, plant part or plant seed as in need of controlling *Sclerotinia sclerotiorum* infection prior to or concurrently with said applying.

DETAILED DESCRIPTION

Figure 1:
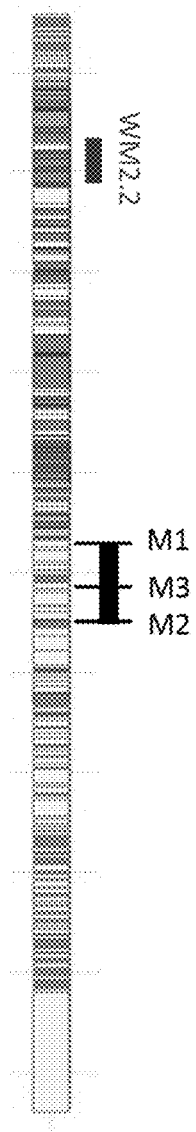
FIG. 1: Shows an overview of *Sclerotinia sclerotiorum* resistance QTLs and marker locations on chromosome 2.

Common bean (*Phaseolus vulgaris* L.) is an important food crop worldwide. There are two main categories of beans sold as food: dry beans and green (or fresh) beans. The agricultural area allocated to each type is different, with 29 million hectare for dry bean and only 2 million hectare for green bean. However, the worldwide production is almost the same, with 24 million tons for dry beans compared to 21 million tons for green beans. The two types of beans are also distinct agronomically. Dry beans and green beans are considered the same species, but the breeding and germplasm are very different since the desired end product for consumption is distinct. The edible product of a dry bean cultivar is the seed from the pod. Dry bean cultivars are developed to produce seeds that are harvested at maturity and generally dried for storage and to increase shelf life. In contrast, green bean cultivars are developed to produce pods that are harvested prior to maturity. The edible product of a green bean cultivar is the immature pod. Dry bean seeds vary significantly in shape, size, and color depending on the type of dry bean. Fresh or green beans generally vary in the size and shape of the pod.

Due to the significant number of differences in the desirable agronomic traits, breeding between the two gene pools generally leads to undesirable intermediate varieties that display traits that may be acceptable in dry beans but are undesirable in green beans. One such trait is seed color. In dry beans, variation in seed color is desirable as the color of the bean is used to distinguish between the bean types. However in green beans, white or colorless seeds are desirable since green beans are often canned and colored seeds will cause the canning liquid to become dark. The white color is the result of the cotyledons shining through a colorless seed coat. Breeders have kept the dry bean and green bean gene pools separate due to the large differences in the agronomic traits considered to be desirable for the two bean types. In fact, introgressing a trait from a dry bean variety into a green bean variety is generally considered similar to introgressing a trait from a wild species. Therefore, certain traits that are important for both types, such as disease resistance, may be present in the dry bean gene pool, but are not transferrable to or available for the green bean gene pool.

White mold disease, which is caused by the fungus *Sclerotinia sclerotiorum*, affects over 400 plant species, including common bean. *Sclerotinia sclerotiorum* thrives in cool to moderate temperatures, which is also the preferred environmental conditions for growing bean crops. Bean cultivars grown in these areas can come under heavy disease pressure, which can lead to crop losses between 30-100%. Management strategies such as fungicide application can be combined with plant architecture traits such as tall, upright growth habit and porous canopy to prevent or reduce infection by *Sclerotinia sclerotiorum* under lower disease pressure. However, when disease pressure increases due to more favorable environmental conditions, these measures are inadequate and it is essential that the bean cultivars include resistance against *Sclerotinia sclerotiorum*. In addition, resistant cultivars reduce and/or eliminate the use of fungicides.

*Sclerotinia sclerotiorum* resistance has been extensively studied in dry bean. All known resistance sources are dry bean varieties and provide quantitative resistance to *Sclerotinia sclerotiorum*. One commonly studied source of *Sclerotinia sclerotiorum* resistance for dry bean is the large-seeded Andean dry bean line G122. The publicly reported QTL regions that are responsible for *Sclerotinia sclerotiorum* resistance in G122 are located on chromosome 2 (WM2.2), chromosome 7 (WM7.1), and chromosome 8 (WM8.3). A QTL on chromosome 1 was also identified but this QTL is believed to relate to disease avoidance associated with a more resilient plant architecture rather than to physiological resistance.

The identification of resistance sources and resistance loci is only a first step in developing resistant varieties. The trait must also be transferred from the source and incorporated into the relevant bean cultivar, which is typically elite material. However, since the genetic distance is high between the different bean types, there is a high likelihood that undesired traits will be transferred along with the desired trait from the source. Miklas et al. reported significant yield loss and other drag phenotypes when attempting to introduce *Sclerotinia sclerotiorum* resistance from G122 into a pinto bean type, which is a small seeded dry bean type. Due to the significant differences between dry bean and green bean, it is likely that significant drag will occur.

Another aspect that further complicates identification of resistance loci is that the results from the greenhouse straw test for white mold resistance and the results from field testing for white mold resistance are not always consistent when compared. The greenhouse straw test and field testing are the two main methods used to assay *Sclerotinia sclerotiorum* resistance. The straw test is often used because it is inexpensive, fast, and high throughput. Field testing provides more realistic conditions, but is more time consuming and less accurate than the straw test. In addition, resistance observed in field tests may result from a combination of physiological resistance and disease avoidance, while the resistance observed in the straw test can be attributed to physiological resistance. It is preferable to identify and validate resistance QTLs through testing using both methods.

Although certain QTLs have been identified from dry bean, these have not been successfully used in green bean due to linkage drag associated with the QTL. In particular, green bean breeders have reported commercially unacceptable seed color due to linkage associated with *Sclerotinia sclerotiorum* resistance introgressions. This is the result of unfavorable alleles tightly linked to the allele of interest. In some cases, it is possible that unfavorable horticultural traits are even caused by the gene of interest. In addition, recombination is often suppressed in regions that are introgressed from wild relatives, especially if those relatives are further removed genetically. In the case of tightly linked deleterious traits the development of markers can help to assist the breeder in overcoming the unfavorable horticultural traits. In addition, recombination events can be developed to provide breeders with smaller introgressions of wild species DNA to be used in a breeding program.

The present inventors have made significant advancements in obtaining *Sclerotinia sclerotiorum* resistance in green beans by identifying novel QTLs on chromosome 2 and chromosome 7 and developing novel recombinant chromosomal segments on chromosome 2 and chromosome 7. These QTLs are distinct from those known in the art. In addition, the inventors have broken the linkage between the resistance and the deleterious seed color trait associated with *Sclerotinia sclerotiorum* resistance. As such, novel chromosomal segments that confer *Sclerotinia sclerotiorum* resistance without the deleterious seed color trait previously associated with *Sclerotinia sclerotiorum* resistance on chromosome 7 are provided. In addition, novel markers for the introgressed alleles are provided, allowing the alleles to be accurately introgressed and tracked during plant breeding. As such, the invention permits introgression of the disease resistance alleles into any desired green bean genotype.

In certain embodiments, plants are provided comprising an introgressed *Sclerotinia sclerotiorum* resistance allele on chromosome 2, wherein said allele confers to said plant increased resistance to *Sclerotinia sclerotiorum* compared to a plant not comprising the allele. In addition, plants are provided comprising an introgressed *Sclerotinia sclerotiorum* resistance allele on chromosome 7, wherein said allele confers to said plant increased resistance to *Sclerotinia sclerotiorum* compared to a plant not comprising the allele. In further embodiments, said resistance allele lacks a deleterious allele genetically linked thereto that confers undesirable seed color to said plant when present. In yet further embodiments, plants are provided comprising combinations of introgressed *Sclerotinia sclerotiorum* resistance alleles on chromosomes 2 and 7, wherein said alleles lacks a deleterious allele genetically linked thereto that confers undesirable seed color to said plant when present.

In some embodiments, said introgressed *Sclerotinia sclerotiorum* resistance allele is defined as located on chromosome 2 within a recombinant chromosomal segment flanked by marker locus M1 (SEQ ID NO: 1) and marker locus M2 (SEQ ID NO: 7). The invention further provides marker locus M3 (SEQ ID NO: 2) as an interstitial marker between markers M1 and M2 that can be used to select the introgressed *Sclerotinia sclerotiorum* resistance allele on chromosome 2. Marker locus M1 comprises a SNP change from A to T at 23,719,195 bp of version 1.0 of the public *P. vulgaris* reference genome sequence, marker locus M2 comprises a SNP change from A to G at 27,452,157 bp of version 1.0 of the *P. vulgaris* reference genome sequence, and marker locus M3 comprises a SNP change from A to G at 25,572,785 bp of version 1.0 of the *P. vulgaris* reference genome sequence.

In some embodiments, the introgressed *Sclerotinia sclerotiorum* resistance allele is defined as located on chromosome 7 within a recombinant chromosomal segment flanked by marker locus M9 (SEQ ID NO: 8) and marker locus M10 (SEQ ID NO: 14) or marker locus M11 (SEQ ID NO: 20) and marker locus M12 (SEQ ID NO: 26). The invention further provides marker locus M4 (SEQ ID NO: 9) as an interstitial marker between markers M9 and M10. The invention further provides marker locus M8 (SEQ ID NO: 21) as an interstitial marker between markers M11 and M12. The invention further provides marker locus M6 (SEQ ID NO: 15) as a marker that can be used to select against the colored seed linkage drag. Marker locus M4 comprises a SNP change from A to G at 2,281,649 bp of version 1.0 of the public *P. vulgaris* reference genome sequence, marker locus M6 comprises a SNP change from T to G at 40,164,131 bp of version 1.0 of the *P. vulgaris* reference genome sequence, marker locus M8 comprises a SNP change from A to C at 42,571,499 bp of version 1.0 of the *P. vulgaris* reference genome sequence, marker locus M9 comprises a SNP change from A to G at 2,031,172 bp of version 1.0 of the *P. vulgaris* reference genome sequence, marker locus M10 comprises a SNP change from A to G at 3,231,059 bp of version 1.0 of the *P. vulgaris* reference genome sequence, marker locus M11 comprises a SNP change from A to G at 42,414,123 bp of version 1.0 of the *P. vulgaris* reference genome sequence, and marker locus M12 comprises a SNP change from A to C at 45,411,236 bp of version 1.0 of the *P. vulgaris* reference genome sequence. The public genome of common bean is available at, for example phaseolus-genes.bioinformatics.ucdavis.edu, and one skilled in the art would understand how to locate the marker sequences provided for the first time in the instant application on any version (or later version) of the public genome.

In other embodiments, the invention provides plants comprising one or more of the novel recombinant introgressions provided herein. These novel introgressions provide robust resistance to *Sclerotinia sclerotiorum*, while avoiding the reduction in performance characteristics associated with conventional introgressions of the *Sclerotinia sclerotiorum* resistance alleles. Methods of producing the plants described herein are further provided. The invention further provides novel trait-linked markers which can be used to produce plants comprising novel recombinant introgressions on chromosomes 2 and 7 conferring *Sclerotinia sclerotiorum* resistance as described herein. In particular embodiments, the invention provides the markers shown in Table 4. Other embodiments of the invention provide markers M1 (SEQ ID NO: 1), M2 (SEQ ID NO: 7), M3 (SEQ ID NO: 2), M9 (SEQ ID NO: 8), M4 (SEQ ID NO: 9), M10 (SEQ ID NO: 14), M6 (SEQ ID NO: 15), M11 (SEQ ID NO: 20), M8 (SEQ ID NO: 21), and M12 (SEQ ID NO: 26), which have been shown to be genetically linked to *Sclerotinia sclerotiorum* resistance in plants.

The invention further provides reduced recombinant introgressions lacking the genomic locus of the *Sclerotinia sclerotiorum* resistance donor at marker locus M6 (SEQ ID NO: 15), wherein said reduced genomic interval lacks deleterious seed color alleles associated with larger *Sclerotinia sclerotiorum* resistance introgressions.

Methods of producing plants comprising the reduced recombinant introgressions described herein are further provided. In some examples, donor DNA from a resistant donor parent is introgressed into a cultivated plant line (the recurrent parent line). M6 (SEQ ID NO: 15) is used to select the allele of the recurrent parent and M11 (SEQ ID NO: 20) and M12 (SEQ ID NO: 26) are used to select the allele of the resistance donor parent resulting in a reduced genomic interval lacking deleterious traits associated with larger *Sclerotinia sclerotiorum* resistance introgressions.

In certain embodiments, the invention provides methods of producing or selecting a green bean plant exhibiting resistance to *Sclerotinia sclerotiorum* comprising: a) crossing a green bean plant provided herein with itself or with a second green bean plant of a different genotype to produce one or more progeny plants; and b) selecting a progeny plant comprising said first introgressed allele or said second introgressed allele. In some embodiments, methods of the invention comprise selecting a progeny plant by detecting nucleic acids comprising marker locus M1 (SEQ ID NO: 1), M2 (SEQ ID NO: 7), M3 (SEQ ID NO: 2), M9 (SEQ ID NO: 8), M4 (SEQ ID NO: 9), M10 (SEQ ID NO: 14), M6 (SEQ ID NO: 15), M11 (SEQ ID NO: 20), M8 (SEQ ID NO: 21), or M12 (SEQ ID NO: 26).

Because genetically diverse plant lines can be difficult to cross, the introgression of *Sclerotinia sclerotiorum* resistance alleles into cultivated lines using conventional breeding methods could require prohibitively large segregating populations for progeny screens with an uncertain outcome. Marker-assisted selection (MAS) is therefore essential for the effective introgression of *Sclerotinia sclerotiorum* resistance alleles into elite cultivars. However, previously known markers for *Sclerotinia sclerotiorum* resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. Genomic Regions, Alleles, and Polymorphisms Associated With *Sclerotinia sclerotiorum* Resistance in Green Bean Plants The invention provides novel introgressions of one or more alleles associated with *Sclerotinia sclerotiorum* disease resistance without the undesirable seed color trait in green bean plants, together with polymorphic nucleic acids and linked markers for tracking the introgressions during plant breeding.

Dry bean lines exhibiting *Sclerotinia sclerotiorum* resistance are known in the art and may be used together with the novel trait-linked markers provided herein in accordance with certain embodiments of the invention. For example, the known and publicly available dry bean lines G122 and A195, can be used as sources for *Sclerotinia sclerotiorum* resistance. G122, which also carries the designations PI 163120 and "Jatu Rong," is publicly available from the U.S. National Plant Germplasm System. A195, which also carries the designation PI 643973, is publicly available from the U.S. National Plant Germplasm System.

Using the improved genetic markers and assays of the invention, the present inventors were able to successfully identify novel reduced introgressions that confer *Sclerotinia sclerotiorum* resistance to the plant with fewer deleterious traits when introgressed into a green bean line. In certain embodiments, the invention provides green bean plants comprising donor DNA between marker locus M1 (SEQ ID NO: 1) and marker locus M2 (SEQ ID NO: 7) on chromosome 2, marker locus M9 (SEQ ID NO: 8) and marker locus M10 (SEQ ID NO: 14) on chromosome 7, or marker locus M11 (SEQ ID NO: 20) and marker locus M12 (SEQ ID NO: 26) on chromosome 7.

The novel introgressions provided herein confer robust resistance to *Sclerotinia sclerotiorum*, while avoiding the undesirable seed color seen with conventional introgressions. The invention therefore represents a significant advance in the art.

II. Introgression of Genomic Regions Associated with *Sclerotinia sclerotiorum* Resistance Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a *Sclerotinia sclerotiorum* resistant plant into a cultivated line. The invention further provides markers for identifying and tracking the novel introgressions disclosed herein during plant breeding, including the markers set forth in Table 1.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Green bean plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Green bean plants comprising an introgressed region comprising regions closely linked to or adjacent to the genomic regions and markers provided herein and associated with a disease resistance phenotype are also provided.

III. Development of Disease Resistant Green Bean Varieties

For most breeding objectives, commercial breeders work with germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated green bean types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and genetically linked deleterious alleles from the non-cultivated parent. For example, non-cultivated green bean types can provide alleles associated with disease resistance. However, these non-cultivated types may have poor horticultural qualities such as poor quality, poor architecture, low yield, or small fruit size.

The process of introgressing desirable resistance genes from non-cultivated lines into elite cultivated lines while avoiding problems with genetically linked deleterious alleles or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the inventors' discovery of accurate markers associated with disease resistance will facilitate the development of green bean plants having beneficial phenotypes. For example, seed can be genotyped using the markers of the present invention to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rina gene in peanut. Meiotic recombination is essential for classical breeding because it enables the transfer of favorable alleles across genetic backgrounds, the removal of deleterious genomic fragments, and pyramiding traits that are genetically tightly linked. Therefore, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among bean species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Marker Assisted Breeding and Genetic Engineering Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) *Genomics*, 8(2), 271-278), denaturing gradient gel electrophoresis (Myers (1985) EPO 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a bean plant a genotype associated with disease resistance, identify a green bean plant with a genotype associated with disease resistance, and to select a green bean plant with a genotype associated with disease resistance. In certain embodiments of methods of the invention, polymorphic nucleic acids can be used to produce a green bean plant that comprises in its genome an introgressed locus associated with disease resistance. In certain embodiments of the invention, polymorphic nucleic acids can be used to breed progeny green bean plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to a condition where the two alleles at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in green bean plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Various genetic engineering technologies have been developed and may be used by those of skill in the art to introduce traits in plants. In certain aspects of the claimed invention, traits are introduced into bean plants via altering or introducing a single genetic locus or transgene into the genome of a variety or progenitor thereof. Methods of genetic engineering to modify, delete, or insert genes and polynucleotides into the genomic DNA of plants are well-known in the art.

In specific embodiments of the invention, improved bean lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a bean plant genome (see, for example Sauer et al., Plant Physiol, 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by back-cros sing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Nat. Biotechnol., 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994), and Ellul et al. (*Theor. Appl. Genet.*, 107:462-469, 2003).

V. Chemical and Biological Treatments

Resistance conferred by the *Sclerotinia sclerotiorum* resistance loci provided herein may be combined with chemical or biological treatments. In one embodiment, the *Sclerotinia sclerotiorum* resistance loci of the present invention may be combined with SERENADE products to produce a surprisingly improved level of protection against *Sclerotinia sclerotiorum*.

The SERENADE products contains a unique strain of *Bacillus subtilis* (strain QST713) and many different lipopeptides that work synergistically to destroy disease pathogens and provide superior antimicrobial activity. The SERENADE products are used to protect plants such as vegetables, fruit, nut and vine crops against diseases such as Fire Blight, Botrytis, Sour Rot, Rust, Sclerotinia, Powdery Mildew, Bacterial Spot and White Mold. The SERENADE products are available as either liquid or dry formulations which can be applied as a foliar and/or soil treatment. Copies of EPA Master Labels for SERENADE products, including SERENADE ASO, SERENADE MAX, SERENADE OPTIMUM (or OPTI), and SERENADE SOIL, are publicly available through National Pesticide Information Retrieval System's (NPIRS®) USEPA/OPP Pesticide Product Label System (PPLS).

SERENADE ASO (Aqueous Suspension-Organic) (EPA Registration No. 264-1152) contains 1.34% of QST713 as an active ingredient and 98.66% of other ingredients. SERENADE ASO is formulated to contain a minimum of $1 \times 10^9$ cfu/g of QST713 while the typical maximum amount of QST713 has been determined to be $3.3 \times 10^{10}$ cfu/g. Some alternate commercial names for SERENADE ASO include SERENADE BIOFUNGICIDE, SERENADE SOIL and SERENADE GARDEN DISEASE.

SERENADE OPTIMUM (or OPTI) contains 26.2% of dried QST713 as an active ingredient and 73.8% of other ingredients. SERENADE OPTIMUM (or OPTI) is formulated to contain a minimum of $1.31 \times 10^{10}$ cfu/g of QST713. For further information, see the U.S. EPA Master Label for SERENADE® OPTIMUM (or OPTI), which is incorporated by reference herein in its entirety.

*Bacillus subtilis* QST713, its mutants, its supernatants, and its lipopeptide metabolites, and methods for their use to control plant pathogens and insects are fully described in U.S. Pat. Nos. 6,060,051; 6,103,228; 6,291,426; 6,417,163; and 6,638,910; each of which is specifically and entirely incorporated by reference herein for everything it teaches. In these U.S. patents, the strain is referred to as AQ713, which is synonymous with QST713. *Bacillus subtilis* QST713 has been deposited with the NRRL on May 7, 1997, under the provisions of the Budapest Treaty on the International Recognition of the Deposit of Microorganisms for the Purpose of Patent Procedure under Accession Number B-21661. Any references in this specification to QST713 refer to *Bacillus subtilis* QST713 (aka AQ713) as present in the SERENADE® products, deposited under NRRL Accession No. B-21661, or prepared in bioreactors or shake flasks under conditions that simulate production of the SERENADE product.

NRRL is the abbreviation for the Agricultural Research Service Culture Collection, an international depositary authority for the purposes of deposing microorganism strains under the Budapest Treaty on the international recognition of the deposit of microorganisms for the purposes of patent procedure, having the address National Center for Agricultural Utilization Research, Agricultural Research Service, U.S. Department of Agriculture, 1815 North University Street, Peoria, Ill. 61604, U.S.A.

At the time of filing U.S. patent application Ser. No. 09/074,870 in 1998, which corresponds to the above patents, the QST713 strain was designated as a *Bacillus subtilis* based on classical, physiological, biochemical and morphological methods. Taxonomy of the *Bacillus* species has evolved since then, especially in light of advances in genetics and sequencing technologies, such that species designation is based largely on DNA sequence rather than the methods used in 1998. After aligning protein sequences from *B. amyloliquefaciens* FZB42, *B. subtilis* 168 and QST713, approximately 95% of proteins found in *B. amyloliquefaciens* FZB42 are 85% or greater identical to proteins found in QST713; whereas only 35% of proteins in *B. subtilis* 168 are 85% or greater identical to proteins in QST713. However, even with the greater reliance on genetics, there is still taxonomic ambiguity in the relevant scientific literature and regulatory documents, reflecting the evolving understanding of *Bacillus* taxonomy over the past 15 years. For example, a pesticidal product based on *B. subtilis* strain FZB24, which is as closely related to QST713 as is FZB42, is classified in documents of the Environmental Protection Agency as *B. subtilis* var. amyloliquefaciens. Due to these complexities in nomenclature, this particular *Bacillus* species is variously designated, depending on the document, as *B. subtilis*, *B. amyloliquefaciens*, and *B. subtilis* var. amyloliquefaciens. Therefore, we have retained the *B. subtilis* designation of QST713 rather than changing it to *B. amyloliquefaciens*, as would be expected currently based solely on sequence comparison and inferred taxonomy. As regulatory authorities in various countries may require registration under any one of the possible taxonomic classifications, it is to be understood for purposes of this patent application that the strain deposited as *Bacillus subtilis* QST713 and assigned NRRL Accession No. B-21661 is equivalent to *Bacillus amyloliquefaciens* QST713.

In one aspect, a fungicidal variant strain of the *Bacillus subtilis* strain QST713 is provided. The term "variant" refers to a genetic variant derived from the *Bacillus subtilis* strain. The variant strain may have, for example, one or more or all of the identifying, functional characteristics of the *Bacillus subtilis* strain QST713. In a particular instance, the variant, as an identifying functional characteristic, reduces *Sclerotinia sclerotiorum* infection at least as well as the parent *Bacillus subtilis* strain QST713. Such variants may be genetic variants having a genomic sequence that has greater than about 85%, greater than about 90%, greater than about 95%, greater than about 96%, greater than about 97%, greater than about 98%, or greater than about 99% sequence identity to *Bacillus subtilis* strain QST713. As used herein, the term "sequence identity" refers to the extent to which two optimally aligned polynucleotide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers the genomic sequence of *Bacillus subtilis* strain QST713. In particular embodiments, fungicidal mutant strains of the *Bacillus subtilis* strain QST713 may be genetic variants having greater than about 90%, 95%, 96%, 97%, 98% or 99% sequence identity over the full length of the genomic sequence of *Bacillus subtilis* strain QST713. Variants may be obtained by treating cells of *Bacillus subtilis* strain QST713 with chemicals or irradiation or by selecting spontaneous mutants from a population of *Bacillus subtilis* strain QST713 cells (such as phage resistant or antibiotic resistant mutants), by genome shuffling, as described below, or by other means well known to those practiced in the art. Multiple rounds of mutagenesis, with and without screening between rounds, may be used to generate and screen mutants.

Genome shuffling among *Bacillus subtilis* strains can be facilitated through the use of a process called protoplast fusion. The process begins with the formation of protoplasts from vegetative bacillary cells. The removal of peptidoglycan cell wall, typically using lysozyme and an osmotic stabilizer, results in the formation of a protoplast. This process is visible under a light microscope with the appearance of spherical cells. Addition of polyethylene glycol (PEG) then induces fusion among protoplasts, allowing genetic contents of two or more cells to come in contact facilitating recombination and genome shuffling. Fused cells then repartition and are recovered on a solid growth medium. During recovery, protoplasts rebuild peptidoglycan cell walls, transitioning back to bacillary shape. See Schaeffer, et al., (1976) PNAS USA, vol. 73, 6:2151-2155).

A "carrier" is defined as any substance or material that may be used and/or combined with a microbial strain or isolate to improve the delivery or effectiveness of the microbial strain or isolate to a plant, plant part or plant seed. An agriculturally acceptable carrier may include a soil-compatible carrier, a seed-compatible carrier, and/or a foliar-compatible carrier. As used herein, the term "soil-compatible carrier" refers to a material that can be added or applied to a soil without causing/having an unduly adverse effect on plant yield, soil structure, soil drainage, or the like. The term "seed-compatible carrier" refers to a material that can be added or applied to a seed without causing/having an unduly adverse effect on the seed, seed germination, the plant that grows from the seed, or the like. The term "foliar-compatible carrier" refers to a material that can be added or applied to an above ground portion of a plant or plant part without causing/having an unduly adverse effect on plant yield, plant health, or the like. Selection of appropriate carrier materials will depend on the intended application(s) and the microorganism(s) present in the composition. The carrier material (s) may be selected and/or combined to provide a composition or formulation in the form of a liquid, gel, slurry, or solid. Compositions may comprise one or more liquid and/or gel carriers, and/or one or more aqueous and/or non-aqueous solvents. As used herein, the term "non-aqueous" may refer to a composition, solvent or substance that comprises no more than a trace amount of water (e.g., no more than 0.5% water by weight).

Containers and kits comprising a microbial composition described herein are further provided. Kits may further include other compositions and instructions for using the microbial composition, such as in conjunction with farming practices. Containers may include bags or other containers or enclosures containing a dry formulation or powder of a microbial composition, and jugs or other containers may contain a liquid formulation of a microbial composition. Further provided are bags or other containers or enclosures that have seeds or other plant materials that have been treated or coated with a microbial composition.

In certain embodiments, methods may comprise applying a composition to a plant, plant part, seed, or growth medium associated therewith. The applying step may comprise, for example, solid matrix priming, imbibing, coating, spraying, tumbling, agitating, dripping, soaking, immersing, dusting, drenching or encapsulating with the composition. In some embodiments, a composition may be applied to a plant, wherein the composition comprises an effective amount of a microbial strain or isolate to increase resistance to white bean mold. A "growth medium" may include soil and any other medium known in the art that permits growth of a plant by providing a medium, matrix or substrate for root growth. A microbial composition may be applied to a growth medium or soil prior to planting, simultaneously with or near the time of planting, such as within the furrow, or after planting (including during later stages of plant growth). According to some embodiments, a microbial composition may be applied directly to the soil at, near or surrounding a planted seed or the root zone of a plant. According to some embodiments, a microbial composition may be applied directly to the foliar tissues (e.g., leaf/leaves, stem, etc.) of a plant.

VI. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which green bean plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of green bean breeding. An "elite population" is an assortment of elite individuals or varieties that can be used to represent the state of the art in terms of agronomically superior genotypes of a given crop species, such as green bean. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to *Sclerotinia sclerotiorum*.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1

Preliminary Mapping of *Sclerotinia sclerotiorum* Resistance in Green Bean

To map *Sclerotinia sclerotiorum* resistance in green bean, a recombinant inbred line (RIL) population was generated from the cross of Valentino, a large-sieve green bean for the fresh and processing market that is susceptible to *Sclerotinia sclerotiorum* with the resistant dry bean line G122. This population was advanced to the $F_6$ generation by single seed descent. Two phenotypic evaluations of the F6:9 families consisting of 281 RILs were included in the QTL analysis. The phenotypic trials were performed in the greenhouse using a random complete block design. In addition, a field trial was conducted with a 3-replication random complete block design. The $F_6$ population was genotyped using a Golden Gate fingerprinting platform. Over 600 markers were identified and mapped to a reference map.

Subsequently, a QTL analysis was performed using a variety of approaches, including single-marker regression, non-parametric interval mapping model, and composite interval mapping. This analysis resulted in two QTL peaks, located on chromosome 2 (WMS_2), chromosome 7 (WMS_7), respectively. There were two QTL peaks on chromosome 7, which are ~25 cM apart from each other. Due to a large gap of ~10 cM in between, there were not enough recombination events to determine if the two peaks represent one large QTL or two smaller separate QTLs. As a result, the accurate positions of these two QTLs are difficult to estimate by either interval mapping or marker regression.

Example 2

Validation of *Sclerotinia sclerotiorum* Resistance Loci

The QTLs on chromosomes 2 and 7 were subsequently validated using the recurrent parent line Valentino. The two peaks located on chromosome 7 were investigated as two separate QTLs (WMS_7.1 and WMS_7.2). Lines containing a single QTL, as well as all possible combinations of QTLs, were developed to validate the effectiveness of single QTLs as well as their level of interaction (Table 1).

TABLE 1

Overview of the lines created to validate the efficacy of the QTLs

|        | WMS_2 | WMS_7.1 | WMS_7.2 |
|--------|-------|---------|---------|
| Line 1 | R     | R       | R       |
| Line 2 | R     | R       | S       |
| Line 3 | R     | S       | R       |
| Line 4 | R     | S       | S       |
| Line 5 | S     | R       | R       |
| Line 6 | S     | R       | S       |
| Line 7 | S     | S       | R       |
| Line 8 | S     | S       | S       |

Each line was developed by backcrossing to the recurrent parent at least 3 times, then selfed at least 3 times, using markers for each backcross and selfing generation to track each QTL. All lines were from the same $BC_3F_2$ plant to ensure maximum similarity of background genotype. All populations were tested using the greenhouse seedling test. Plants were inoculated ~9 days after planting and scored for disease ~33 days after planting. The experimental design was a randomized complete block design with 36 reps, where each rep was one tray on a bench containing 12 pots, with one plant per pot. In addition, the lines were also tested using the greenhouse straw test. For this experiment, the design was a randomized complete block design with 18 reps, one pot per entry per rep, with the pot containing two subsamples that were averaged to give a *Sclerotinia sclerotiorum* resistance score. In this test, plants are scored at an older stage than in the seedling test, but younger than plants scored in the field trial.

Analysis of the data was performed using SAS/JMP software. An ANOVA was run on each QTL to determine the significance of effect on *Sclerotinia sclerotiorum* resistance, with the QTL as a fixed effect and the rep as a random effect. The percent of variation explained by each QTL, by rep, and by error, was estimated using PROC VARCOMP. LS Means of individual QTLs and QTL combinations were compared to assess additive effects. All three QTLs were confirmed in the greenhouse setting (Table 2).

TABLE 2

Summary of validation results for the greenhouse experiment

|                        | WMS_2     | WMS_7.1   | WMS_7.2   |
|------------------------|-----------|-----------|-----------|
| Validation Background  | Valentino | Valentino | Valentino |
| Significant?           | Yes       | Yes       | Yes       |
| $R^2$                  | 47%       | 9%        | 35%       |

The eight fixed $BC_3F3$ lines were tested in the field. In addition to the original background line Valentino, a second background line, PINDJV1012 (a Pinto type dry bean line), was used to validate the QTLs. Lines having the PINDJV1012 background were created in the same way as those having the Valentino background. Since each entry is a sibling from the same $BC_3F_2$ plant, the entries are "Near Isogenic Lines," meaning they should contain the same genetic background and only vary at the QTL. This was confirmed using fingerprinting. The lines were screened in the field in a randomized complete block design experiment with 10 replications. Plots were ~10' in length and sown with 60 seed per plot. Scoring was done on green plants with developing beans (a few weeks after flowering) on a per plot (not per plant) basis on a 1-9 scale, with 1 being total resistance and 9 being complete susceptibility (total death of plot). An ANOVA was run in JMP to determine whether each QTL was significant. A mixed model was used including all QTLs to determine whether any multiplicative effects (QTL interactions) were occurring to indicate epistatic effects. No QTL interactions were observed. In the field setting, only the WMS_2 on chromosome 2 and WMS_7.1 on chromosome 7 could be confirmed (Table 3).

TABLE 3

Summary of the validation experiment in the field

|                        | WMS_2              | WMS_7.1            | WMS_7.2            |
|------------------------|--------------------|--------------------|--------------------|
| Validation Background  | Pinto, Valentino   | Pinto, Valentino   | Pinto, Valentino   |
| Significant?           | Yes, Yes           | Yes, No            | No, No             |
| $R^2$                  | 41-48%             | 30%                | —                  |

Example 3

Fine Mapping of Identified *Sclerotinia sclerotiorum* Resistance Loci

After validating the resistance loci, a mapping population was created to further define the QTL regions on chromosome 2 and on chromosome 7. For the QTL on chromosome 2, the Valentino (susceptible parent)×G122 (resistance donor) cross was used to develop a $BC_4F3$ population and families that showed recombination events within the rough mapped QTL regions were selected. To avoid the influence of epistatic effects between resistance loci, only populations having one resistance locus were used for mapping. The selected lines were fixed through selfing to create near-isogenic sister lines (NILs). 14 sister lines were chosen for analysis. These lines were phenotyped for *Sclerotinia sclerotiorum* resistance using the straw method in the greenhouse. Further genotyping identified a genomic region between markers M1 (SEQ ID NO: 1) and M2 (SEQ ID NO: 7) that conferred the resistance to *Sclerotinia sclerotiorum* (FIG. 1). Marker M3 (SEQ ID NO: 2) was identified as a trait-linked marker for selection of the resistance locus on chromosome 2.

Figure 2:
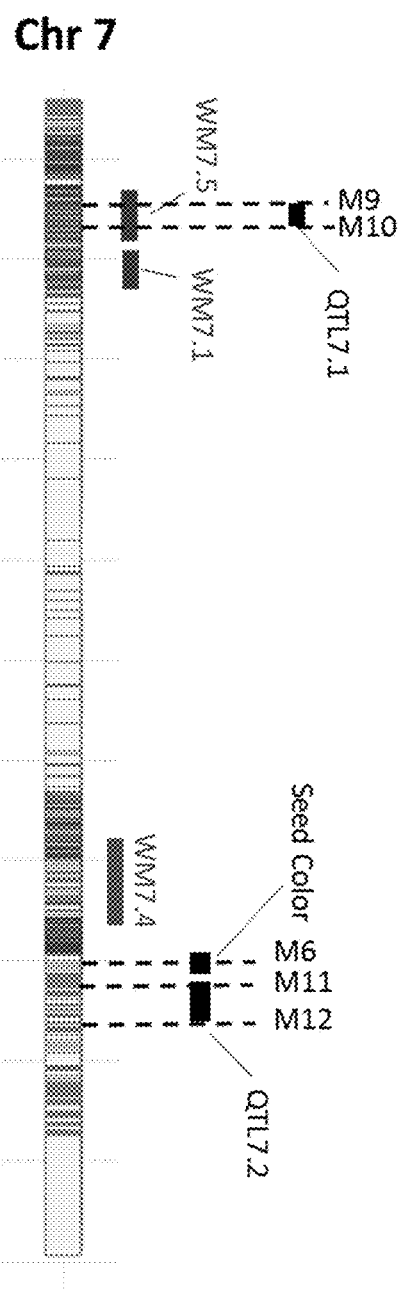
FIG. 2: Shows an overview of *Sclerotinia sclerotiorum* resistance QTLs and marker locations on chromosome 7.

Further mapping of the loci on chromosome 7 was done through a comparative analysis within lines. 26 lines were selected from the $BC_3F5$ generation that were heterozygous in the region that encompasses both QTLs on chromosome 7. These lines were selfed to generate a $BC_3F_6$ generation and for each line two selections were kept for further analysis. These selections were lines in which one line was homozygous for the resistant donor allele and the other line was homozygous for the susceptible parent allele in that location. These 'mirror' lines were then phenotyped for their level of *Sclerotinia sclerotiorum* resistance. Subsequently, the fine mapped location of the resistance QTL on chromosome 7 was determined by comparing the recombination breakpoint in pairs that differed significantly in their *Sclerotinia sclerotiorum* resistance with the breakpoint in those that did not differ significantly. This led to two significant QTL regions on chromosome 7 (FIG. 2). The first (designated WMS_7.1) is located between markers M9 (SEQ ID NO: 8) and M10 (SEQ ID NO: 14) and the second (designated WMS_7.2) is located between markers M11 (SEQ ID NO: 20) and M12 (SEQ ID NO: 26). In addition, marker M4 (SEQ ID NO: 9) was found within the QTL region of WMS_7.1, while marker M8 (SEQ ID NO: 21) was found within the QTL region of WMS_7.2. Markers M4 and M8 can be used in addition to the boundary markers to select for the resistance QTLs.

Example 4

Removal of Deleterious Seed Color Trait

32 $BC_5F_3$ lines (Valentino/G122) and 22 $BC_3F_3$ lines (Golddust/G122) were developed for breeding using *Sclerotinia sclerotiorum* resistance markers on chromosomes 2 and 7. These lines were tested for horticultural traits and *Sclerotinia sclerotiorum* resistance using the greenhouse straw test. It was found that 49 of these events had a dark seed phenotype while only 5 events had the desirable white seed phenotype. Subsequently, all the $F_9$ Valentino/G122 lines in the RIL population used to map the *Sclerotinia sclerotiorum* resistance QTLs from G122 were phenotyped for seed color. It was found that the seed color locus is closely linked to QTL WMS_7.2 on chromosome 7 (FIG. 2). The marker, M6 (SEQ ID NO: 15), was 97% predictive of white seed coat color (TT) and 100% predictive of non-white seed coat color (GG or GT).

Marker M6 was also tested in a diverse panel of 265 inbred lines to determine the predictability of the marker in a broader population. Marker M6 was found to be 94% predictive of the white seed coat color phenotype but was only 46% predictive of the non-white seed coat color phenotype. In a subsequent panel of 138 lines, including material from both the A195 and G122 donors, a 100% predictive efficacy of marker M6 for white/non-white seed coat color was observed. The marker is therefore most effective for breaking the color linkage from the *Sclerotinia sclerotiorum* resistance QTLs on chromosome 7. Markers for tracking the resistance QTLs and seed color phenotype are shown in Table 4.

Example 5

Identification of Alternative Sources of *Sclerotinia sclerotiorum* Resistance

*Sclerotinia sclerotiorum* resistance QTLs were identified and mapped in resistant line A195. A195 is a dry bean variety developed by Shree Singh (Singh et al., 2007). Previous work in dry bean showed that A195 contains two independent complementary genes controlling resistance to *Sclerotinia sclerotiorum* and that there is one dominant resistance gene difference between G122 and A195 (Viteri & Singh, 2015). To assess the efficacy of *Sclerotinia sclerotiorum* resistance from A195 in green bean, a cross was made between A195 and the green bean line "Banga". Recombinant inbred populations were developed and the QTL analysis was performed on the F7:8 populations. The populations were phenotyped using a greenhouse assay. The genotyping was performed using a high-throughput genotyping system utilizing over 3000 markers. $F_8$ bulk seed from 138 families were screened to determine $F_7$ genotypes. Of the 3000+ markers, 1205 were informative and used in the subsequent QTL analysis. The QTL analysis identified two QTLs: one on chromosome 2 at the same location as the G122 locus on chromosome 2 and one on chromosome 7. The QTL on chromosome 7 spanned a large region covering both the WMS_7.1 and WMS_7.2 regions found in G122.

To determine if the resistance QTLs of A195 and those of G122 are different, a comparative genotyping study was performed. This study showed that A195 was identical over a range of 260 markers on chromosome 7, including the resistance QTL regions. This indicates that the resistance QTLs of A195 and G122 are identical on chromosome 7. Similar results were found for the *Sclerotinia sclerotiorum* resistance QTL WMS_2 on chromosome 2.

Example 6

Combination of *Sclerotinia sclerotiorum* Resistance Loci with Chemical or Biological Treatments Resistance conferred by the *Sclerotinia sclerotiorum* resistance loci described herein may be combined with

TABLE 4

List of markers and favorable alleles at each marker for tracking resistance QTLs and seed color

| Marker name | Chr. | Genetic Position (cM) | Public position marker (bp) | Public position SNP (bp) | Marker size (bp) | SNP change | Favorable allele | Marker sequence (SEQ ID NO) | Fwd primer (SEQ ID NO) | Rev primer (SEQ ID NO) | Probe 1 (SEQ ID NO) | Probe 2 (SEQ ID NO) |
|---|---|---|---|---|---|---|---|---|---|---|---|---|
| M1 | 2 | 46.49 | 23,719,154-23,719,255 | 23,719,195 | 101 | [A/T] | T (G122) | 1 | | | | |
| M3 | 2 | 48.23 | 25,572,635-25,572,935 | 25,572,785 | 301 | [A/G] | A (G122) | 2 | 3 | 4 | 5 | 6 |
| M2 | 2 | 50.43 | 27,451,992-27,452,228 | 27,452,157 | 237 | [A/G] | A (G122) | 7 | | | | |
| M9 | 7 | 29.72 | | 2,031,172 | 121 | [A/G] | A (G122) | 8 | | | | |
| M4 | 7 | 31.74 | 2,281,589-2,281,709 | 2,281,649 | 121 | [A/G] | G (G122) | 9 | 10 | 11 | 12 | 13 |
| M10 | 7 | 38.42 | | 3,231,059 | 121 | [A/G] | G (G122) | 14 | | | | |
| M6 | 7 | 59.07 | 40,164,095-40,164,190 | 40,164,131 | 97 | [T/G] | T (white) | 15 | 16 | 17 | 18 | 19 |
| M11 | 7 | 63.40 | | 42,414,123 | 326 | [A/G] | G (G122) | 20 | | | | |
| M8 | 7 | 64.03 | 42,571,439-42,571,559 | 42,571,499 | 121 | [A/C] | C (G122) | 21 | 22 | 23 | 24 | 25 |
| M12 | 7 | 69.45 | | 45,411,236 | 121 | [A/C] | A (G122) | 26 | | | | | chemical or biological treatments. The following example shows that the *Sclerotinia sclerotiorum* resistance loci of the present invention may be combined with SERENADE products to produce a surprisingly improved level of protection against *Sclerotinia sclerotiorum*.

SERENADE acts as a fungicide but may also foster a plant-microbe interaction to positively affect such factors as plant biomass, root growth, defense response pathway activation, improved plant nutrient uptake and activation of plant stress tolerance pathways. SERENADE may be applied through foliar or soil application to assist in the control of white mold infection.

Two types of tests were used to evaluate the effect applying SERENADE to plants comprising the *Sclerotinia sclerotiorum* resistance loci of the present invention. In the first, a straw test, a 50% SERENADE droplet was applied to the cut stem of susceptible or resistant (comprising the *Sclerotinia sclerotiorum* resistance loci) bean plants prior to application of a white mold-agar plug. The plants were then covered with a straw and allowed to incubate for 5, 7, 12, and 20 days. The severity of the infection was evaluated based on a 1-9 rating scale. The results showed a surprisingly unexpected level of protection against white bean mold when SERENADE was applied to bean plants comprising the *Sclerotinia sclerotiorum* resistance loci. The severity of infection was significantly reduced with both 4 g/l and 8 g/l SERENADE application, and the effects of both the SERENADE treatment and the *Sclerotinia sclerotiorum* resistance loci were significant as early as 5 days post inoculation and remained visible until 20 days post inoculation.

In the second, a detached leaf test, detached leaves from a susceptible (S) and two different lines with *Sclerotinia sclerotiorum* resistance-conferring loci (R1 and R2) were evaluated for disease lesion size following inoculation with *Sclerotinia sclerotiorum*. The untreated control (UTC) plant was not sprayed. Treatments of SERENADE were applied at either 4 g/l or 8 g/l whole plant spray, weekly for 4 weeks. Detached leaves were placed in trays and each leaf was inoculated twice with filter paper containing liquid inoculum at either a density of OD600=0.1 or OD600=0.05. Treatment effect was highly significant at 4 days post inoculation for both inoculum densities. SERENADE suppressed the size and number of lesions in S, R1, and R2 germplasm. Reduced infection was observed in R1 and R2 germplasm when compared with S germplasm and in SERENADE treated germplasm when compared with UTC germplasm. The higher concentration of SERENADE application (8 g/l) consistently reduced infection more than the lower concentration (4 g/l). The results again showed a surprisingly unexpected level of protection against white bean mold when SERENADE was applied to bean plants comprising the *Sclerotinia sclerotiorum* resistance loci.

What is claimed is:

1. A kit comprising:
   (a) a green bean plant, plant part thereof, or plant seed thereof comprising a recombinant chromosomal segment on chromosome 2 or chromosome 7, wherein said recombinant chromosomal segment comprises an allele conferring resistance to *Sclerotinia sclerotiorum* relative to a plant, plant part thereof, or plant seed thereof lacking said recombinant chromosomal segment, and wherein:
      (i) said recombinant chromosomal segment on chromosome 2 comprises a marker locus selected from the group consisting of a marker locus M1 (SEQ ID NO: 1), marker locus M2 (SEQ ID NO: 7), and marker locus M3 (SEQ ID NO: 2); or
      (ii) said recombinant chromosomal segment on chromosome 7 comprises marker locus M9 (SEQ ID NO: 8) and marker locus M10 (SEQ ID NO: 14) or marker locus M11 (SEQ ID NO: 20) and marker locus M12 (SEQ ID NO: 26); and
   (b) at least one cell of *Bacillus subtilis* strain QST713, wherein the combination of said *Sclerotinia sclerotiorum* resistance allele and said at least one cell of *Bacillus subtilis* strain QST713, confers to a green bean plant, plant part thereof, or plant seed thereof improved resistance to *Sclerotinia sclerotiorum*.

2. The kit of claim 1, wherein said green bean plant, plant part thereof, or plant seed thereof comprises a first recombinant chromosomal segment on chromosome 2 and a second recombinant chromosomal segment on chromosome 7, wherein said first and second recombinant chromosomal segments comprise an allele conferring resistance to *Sclerotinia sclerotiorum* relative to a plant, plant part thereof, or plant seed thereof lacking said recombinant chromosomal segment.

3. The kit of claim 2, wherein said second recombinant chromosomal segment on chromosome 7 lacks a deleterious allele genetically linked thereto that confers an undesirable color to a seed produced by the plant, and wherein said second recombinant chromosomal segment on chromosome 7 comprises a favorable allele associated with desirable seed color at marker locus M6 (SEQ ID NO: 15).

4. The kit of claim 3, wherein said second recombinant chromosomal segment on chromosome 7 comprises a favorable allele associated with *Sclerotinia sclerotiorum* resistance at marker locus M11 (SEQ ID NO: 20) and marker locus M12 (SEQ ID NO: 26) on chromosome 7.

5. The kit of claim 1, wherein said *Sclerotinia sclerotiorum* resistance allele is located between 23,719,195 bp and 27,452,157 bp on chromosome 2 of the *P. vulgaris* reference genome sequence v. 1.0.

6. The kit of claim 1, wherein said recombinant chromosomal segment comprises a marker locus selected from the group consisting of marker locus M11 (SEQ ID NO: 20), marker locus M8 (SEQ ID NO: 21), and marker locus M12 (SEQ ID NO: 26) on chromosome 7.

7. The kit of claim 1, wherein said recombinant chromosomal segment on chromosome 7 lacks a deleterious allele genetically linked thereto that confers an undesirable color to a seed produced by the plant, and wherein said recombinant chromosomal segment on chromosome 7 comprises a favorable allele associated with desirable seed color at marker locus M6 (SEQ ID NO: 15).

8. The kit of claim 7, wherein said recombinant chromosomal segment on chromosome 7 comprises a favorable allele associated with *Sclerotinia sclerotiorum* resistance at marker locus M11 (SEQ ID NO: 20) and marker locus M12 (SEQ ID NO: 26) on chromosome 7.

9. The kit of claim 1, wherein said *Sclerotinia sclerotiorum* resistance allele is located between 42,414,123 bp and 45,411,236 bp on chromosome 7 of the *P. vulgaris* reference genome sequence v. 1.0.

10. The kit of claim 1, wherein said cell is comprised in an agriculturally acceptable carrier.

11. The kit of claim 10, wherein the agriculturally acceptable carrier is a liquid, gel, slurry, or powder.

12. The kit of claim 1, wherein said kit comprises a seed.

13. The kit of claim 12, wherein said seed comprises a coating comprising said at least one cell of *Bacillus subtilis* strain QST713.

14. A composition comprising:
(a) a green bean plant, plant part thereof, or plant seed thereof comprising a recombinant chromosomal segment on chromosome 2 or chromosome 7, wherein said recombinant chromosomal segment comprises an allele conferring resistance to *Sclerotinia sclerotiorum* relative to a plant, plant part thereof, or plant seed thereof lacking said recombinant chromosomal segment, and wherein:
 (i) said recombinant chromosomal segment on chromosome 2 comprises a marker locus selected from the group consisting of a marker locus M1 (SEQ ID NO: 1), marker locus M2 (SEQ ID NO: 7), and marker locus M3 (SEQ ID NO: 2); or
 (ii) said recombinant chromosomal segment on chromosome 7 comprises marker locus M9 (SEQ ID NO: 8) and marker locus M10 (SEQ ID NO: 14) or marker locus M11 (SEQ ID NO: 20) and marker locus M12 (SEQ ID NO: 26); and
(b) at least one cell of *Bacillus subtilis* strain QST713, wherein the combination of said *Sclerotinia sclerotiorum* resistance allele and said at least one cell of *Bacillus subtilis* strain QST713, confers to a green bean plant, plant part thereof, or plant seed thereof improved resistance to *Sclerotinia sclerotiorum*.

15. The composition of claim 14, wherein said cell is comprised in an agriculturally acceptable carrier.

16. A green bean plant, plant part thereof, or plant seed thereof having applied or coated on at least a portion of the green bean plant, plant part thereof, or plant seed thereof a composition comprising at least one cell of *Bacillus subtilis* strain QST713, wherein said plant, plant part thereof, or plant seed thereof comprises a recombinant chromosomal segment on chromosome 2 or chromosome 7, wherein said recombinant chromosomal segment comprises an allele conferring resistance to *Sclerotinia sclerotiorum* relative to a plant, plant part thereof, or plant seed thereof lacking said recombinant chromosomal segment, and wherein:
(a) said recombinant chromosomal segment on chromosome 2 comprises a marker locus selected from the group consisting of a marker locus M1 (SEQ ID NO: 1), marker locus M2 (SEQ ID NO: 7), and marker locus M3 (SEQ ID NO: 2); or
(b) said recombinant chromosomal segment on chromosome 7 comprises marker locus M9 (SEQ ID NO: 8) and marker locus M10 (SEQ ID NO: 14) or marker locus M11 (SEQ ID NO: 20) and marker locus M12 (SEQ ID NO: 26).

17. The green bean plant, plant part thereof, or plant seed thereof of claim 16, wherein said composition comprises an agriculturally acceptable carrier.

18. A method for controlling *Sclerotinia sclerotiorum* infection, the method comprising applying a composition comprising at least one cell of *Bacillus subtilis* strain QST713, to a green bean plant, plant part thereof, or plant seed thereof, or a growth medium associated with said green bean plant, plant part thereof, or plant seed thereof; wherein said plant, plant part thereof, or plant seed thereof comprises a recombinant chromosomal segment on chromosome 2 or chromosome 7; wherein said recombinant chromosomal segment comprises an allele conferring resistance to *Sclerotinia sclerotiorum* relative to a plant lacking said recombinant chromosomal segment, wherein:
(i) said recombinant chromosomal segment on chromosome 2 comprises a marker locus selected from the group consisting of a marker locus M1 (SEQ ID NO: 1), marker locus M2 (SEQ ID NO: 7), and marker locus M3 (SEQ ID NO: 2); or
(ii) said recombinant chromosomal segment on chromosome 7 comprises marker locus M9 (SEQ ID NO: 8) and marker locus M10 (SEQ ID NO: 14) or marker locus M11 (SEQ ID NO: 20) and marker locus M12 (SEQ ID NO: 26),
and wherein the combination of said *Sclerotinia sclerotiorum* resistance allele and said at least one cell of *Bacillus subtilis* strain QST713 confers to said green bean plant, plant part thereof, or plant seed thereof improved resistance to *Sclerotinia sclerotiorum*.

19. The method of claim 18, wherein the growth medium is soil.

20. The method of claim 19, wherein said soil is located in a field in which said plant or seed is planted.

21. The method of claim 20, wherein the composition is applied to the growth medium before, simultaneously with, or after the plant or plant seed is planted in the growth medium.

22. The method of claim 18, wherein said applying comprises solid matrix priming, imbibing, coating, spraying, tumbling, agitating, dripping, soaking, immersing, dusting, drenching or encapsulating with the composition.

23. The method of claim 18, wherein said applying comprises applying directly to the foliar tissues of a plant.

24. The method of claim 18, wherein said composition is a liquid, gel, slurry, or powder.

25. The method of claim 18, further defined as comprising identifying said bean plant, plant part thereof, or plant seed thereof as in need of controlling *Sclerotinia sclerotiorum* infection prior to or concurrently with said applying.

\* \* \* \* \*